(12) United States Patent
Scott et al.

(10) Patent No.: US 9,402,624 B1
(45) Date of Patent: Aug. 2, 2016

(54) BONE FIXATION STAPLE

(71) Applicants: Joshua Scott, Houston, TX (US); Perry Forrester, Houston, TX (US)

(72) Inventors: Joshua Scott, Houston, TX (US); Perry Forrester, Houston, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 261 days.

(21) Appl. No.: 14/205,551

(22) Filed: Mar. 12, 2014

Related U.S. Application Data

(60) Provisional application No. 61/784,463, filed on Mar. 14, 2013.

(51) Int. Cl.
*A61B 17/06* (2006.01)
*A61B 17/064* (2006.01)

(52) U.S. Cl.
CPC .......... *A61B 17/0642* (2013.01); *A61B 17/064* (2013.01)

(58) Field of Classification Search
CPC .......................... A61B 17/064; A61B 17/0642
See application file for complete search history.

(56) References Cited

U.S. PATENT DOCUMENTS

| | | | |
|---|---|---|---|
| 2009/0062800 A1* | 3/2009 | Shano | A61B 17/0642 606/75 |
| 2009/0177201 A1* | 7/2009 | Soltz | A61B 17/064 606/75 |
| 2012/0080503 A1* | 4/2012 | Woodard, Jr. | A61B 17/064 227/181.1 |
| 2013/0030438 A1* | 1/2013 | Fox | A61B 17/0642 606/75 |

* cited by examiner

*Primary Examiner* — Andrew Yang
(74) *Attorney, Agent, or Firm* — Bushman Werner, P.C.

(57) ABSTRACT

A memory metal bone staple having a metal grain which runs longitudinally along the legs and bridge of the staple. The staple has barbed retaining features and no sharp or abrupt corners on its outer edges.

31 Claims, 3 Drawing Sheets

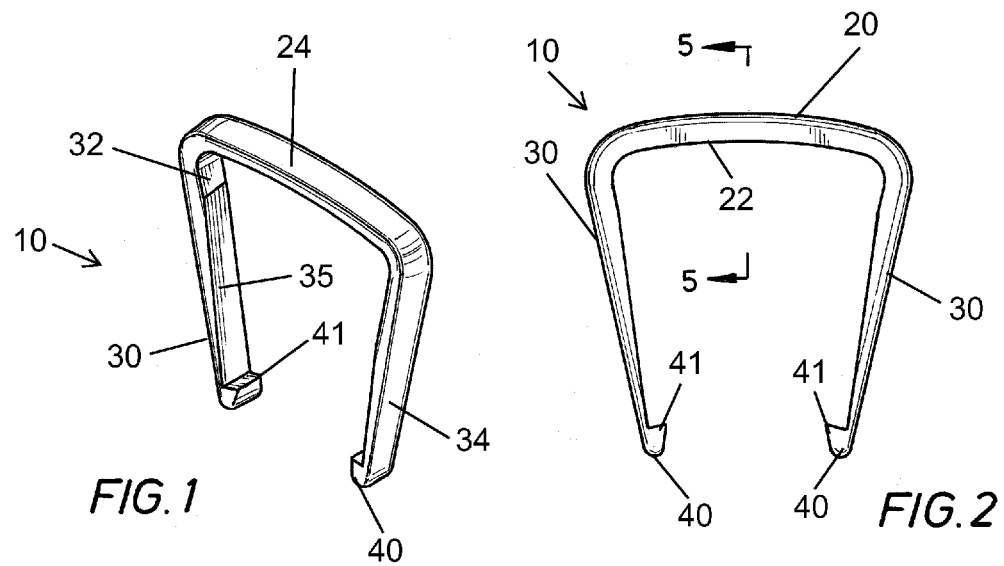
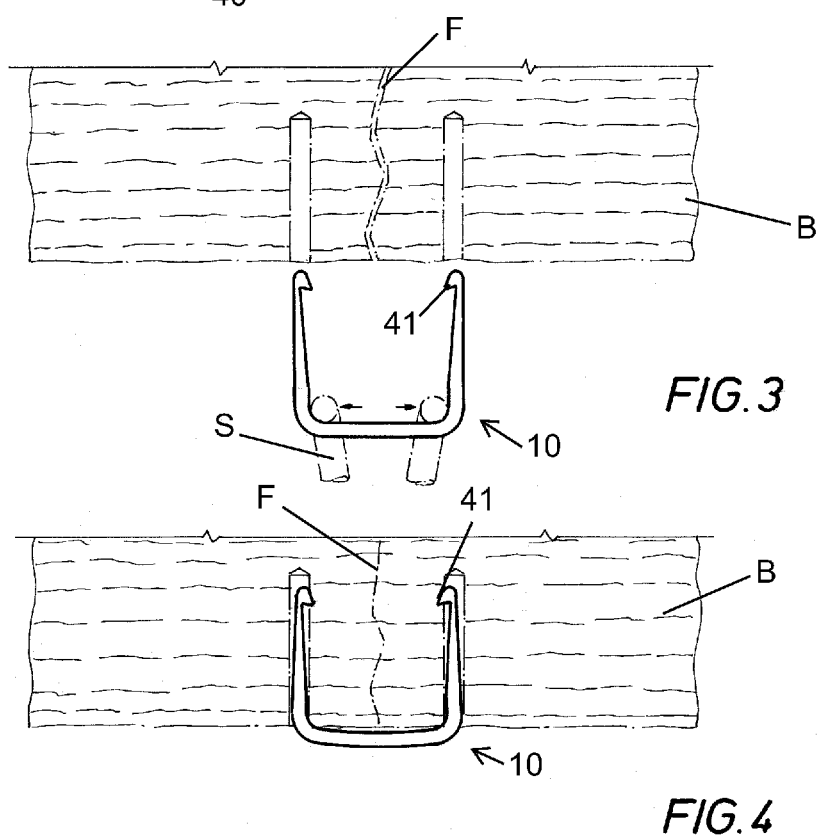

BONE FIXATION STAPLE

CROSS REFERENCE TO RELATED APPLICATION

This application claims priority to U.S. Application No. 61/784,463 filed on Mar. 14, 2013, the disclosure of which is incorporated herein by reference for all purposes.

FIELD OF THE INVENTION

The present invention relates to orthopedic staples used for bone fixation. In particular, the present invention relates to orthopedic staples comprised of nickel/titanium alloy.

BACKGROUND OF THE INVENTION

The use of orthopedic staples, or bone staples, is a common method of bone fixation in orthopedic surgery. A particular type of bone staple is known as the memory staple. Memory staples are comprised of a nickel/titanium alloy, also known as Nitinol. Nickel/titanium alloy is unique in that it undergoes a phase transformation in its crystal structure, changing between the stronger austenite form to the weaker martensite form, when exposed to certain environmental stimuli, e.g., heat or stress. Memory metal made from nickel/titanium alloy is categorized as either shape memory or super elastic. Shape memory metal responds to changes in temperature whereas super elastic metal responds to stress or force applied to the metal. When a shape memory alloy is at cooler temperatures, it is in its martensitic form. The martensitic form is easily deformed to a new shape. However, when the alloy is heated through its transformation temperatures, it reverts to austenite and recovers its previous shape with great force.

Bone staples are generally U-shaped, having a bridge and first and second legs extending from respective sides of the bridge. Bone staples formed from shape memory nickel/titanium alloy are formed at high temperatures with the legs of the staple angled inwardly. The staples are then cooled and stored with the staple legs maintained in an open position, roughly perpendicular to the staple bridge. When the shape memory staples are inserted into the bone of the patient, the bridge spanning the bone fracture, the body temperature of the patient warms the alloy causing it to return to its austensitic form and thus its original shape, with the legs angled inwardly. The staple legs thus exert a compressive force to urge the portions of the bone on opposite sides of the fracture toward each other, which ensures better bone fusion and retards backing out of the staple.

Memory metal can also be super elastic. This unique alloy shows super elastic behavior if deformed at a temperature which is slightly above its transformation temperature. Super elastic bone staples are produced with the staple legs angled inwardly. During insertion of the staple, the staple legs are opened using a staple spreader, and the staple is then inserted into the patient's bone. As soon as the force of the staple spreader is removed from the staple legs, the super elastic metal returns the staple to its original shape with the staple legs angled inward. Again, this results in compressive force on the bone by the staple legs.

Bone stapes today are produced both in shape memory and super elastic forms. In particular, when manufacturing prior art super elastic staples, an ingot of nickel/titanium alloy is first rolled into a flat sheet. The rolling of the metal into a flat sheet results in the formation of grain lines in the metal, much like the grain lines found in wood. The staples cut from the sheets thus have grain lines as well. The shape of the staples cut from the sheet is such that the grain lines of the metal will run generally transverse to the longitudinal axes of the staple's bridge, legs, or both. Grain lines which run transverse or perpendicular to the staple at the intersections between the longitudinal axes of the bridge and/or legs magnify stresses at these intersections in the super elastic staples which can lead to failures or at least reduced ability of the staple to be manipulated freely without fear of failure.

SUMMARY OF THE INVENTION

In one aspect, the present invention provides a super elastic staple having a metal grain which runs along the longitudinal axes of both the legs and bridge of the staple.

In another aspect, the present invention provides a super elastic staple having a metal grain which runs along the longitudinal axes of both the legs and bridge and has barbed retaining features.

In still another aspect, the present invention provides a super elastic staple having no sharp or abrupt corners or edges on its outer surfaces.

These and further features and advantages of the present invention will become apparent from the following detailed description, wherein reference is made to the figures in the accompanying drawings.

BRIEF DESCRIPTION OF THE DRAWINGS

FIG. 1 is an isometric view of one embodiment of the staple of the present invention.

FIG. 2 is a front, elevational view of the staple shown in FIG. 1.

FIG. 3 is an environmental view of the staple of the present invention being opened prior to insertion in a fractured bone.

FIG. 4 is a view similar to FIG. 3 but showing the staple inserted in a bone.

FIG. 9 is a side, elevational view of a staple blank used for forming the staple shown in FIG. 1, and showing how the grain lines of the metal run along the length of the blank.

FIG. 10 is a view, similar to FIG. 2, but showing schematically the grain lines of the metal running longitudinally along the bridge and legs of the staple.

DETAILED DESCRIPTION OF PREFERRED EMBODIMENTS

Figure 5:
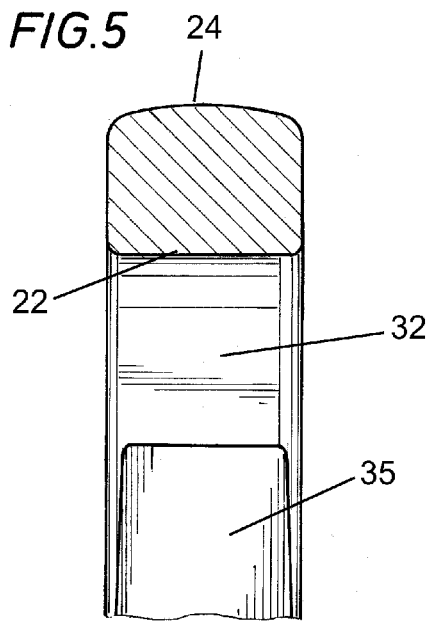
FIG. 5 is a cross-sectional view taken along the lines 5-5 of FIG. 1.

As explained above memory metal comprises shape memory metal and super elastic memory metal. Although described with respect to super elastic metal, it will be understood that the staple of the present invention can also be formed from shape memory metal.

Turning to FIGS. 1 and 2, there is shown a staple, shown generally as 10, having a bridge 20, and legs 30. Bridge 20 comprises inner surface 22 and outer surface 24. It will be understood, for reasons explained more fully hereafter, that the distance between surfaces 22 and 24 constitutes the maximum thickness of the staple 10. Legs 30 comprise inner surface 32, outer surface 34, and terminate in feet 40, having laterally inwardly directed barbs 41. At least a portion of each inner surface 32 is tapered to form tapered surfaces 35 In the relaxed position, legs 30 of staple 10 are angled generally inwardly, as shown in FIGS. 1 and 2. In a preferred embodiment, bridge 20 is slightly arcuate (see FIG. 2).

As seen in FIG. 3, during insertion into a bone B having a fracture F, the surgeon uses a spreader S to open legs 30 of staple 10 to an angle substantially perpendicular to bridge 20. The opening of legs 30 of staple 10, flattens arcuate bridge 20. Thus, the normally arcuate shape of bridge 20 is preferred. If bridge 20 were simply flat, pulling legs 30 open could cause bridge 20 to bow inwardly and press against bone B. As seen in FIG. 4, after insertion into bone B such that staple 10 bridges fracture F, staple 10 is released from the spreader. The legs 30 then move back toward their original, relaxed position. The force of the legs 30 returning to their inwardly angled position exerts a compressive force on both sides of fracture F. As well, the barbs 41 of feet 40 are pressed into bone B and thus provide resistance to the staple backing out.

Turning to FIG. 5, a transverse cross-section of one embodiment of the staple bridge can be seen. Because staple 10 is formed from extruded wire, it can be easily formed with virtually any desired cross-sectional configuration. Thus the outer surface edges can be rounded without the necessity for further working of the staple. In contrast, prior art staples which are typically cut from sheets have straight edges, forming 90° angles when viewed in cross-section. This can be a problem as patients will often rub the staples through the skin during the healing process. Staples having sharp edges on the outer surfaces cause irritation to the patient's skin as a result of this rubbing. Accordingly, many manufacturers of prior art stamped or laser cut staples will round the edges of the staples by placing the staples in a tumbling media. This tumbling step abrades and polishes the edges of the staples to provide more rounded edges. Unfortunately, the process impacts the entire surface area of the staple, thus rounding off any barbs and inner surfaces which perform better when sharp. In contrast, in the present invention the shape of the outer and inner surfaces of staple 10 can be customized simply by changing the shape of the die through which the wire is extruded.

Figure 6:
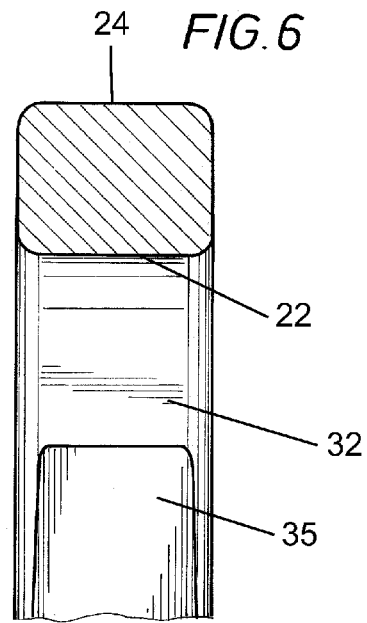
FIG. 6 is a view similar to that shown in FIG. 5, showing an alternate cross-section of the staple of the present invention.
Figure 7:
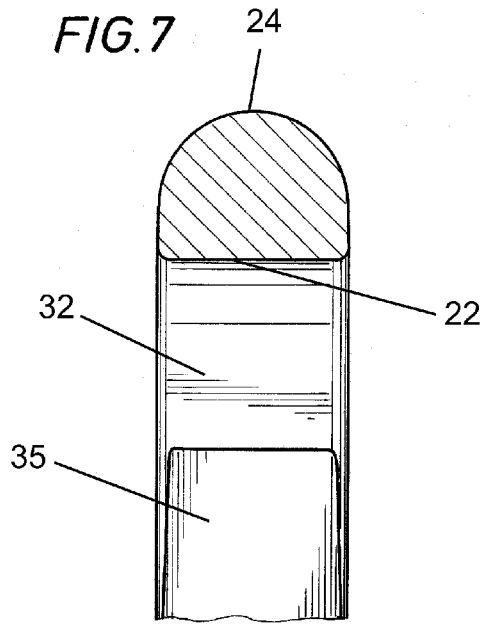
FIG. 7 is a view similar to that shown in FIG. 5, showing an alternate cross-section of the staple of the present invention.
Figure 8:
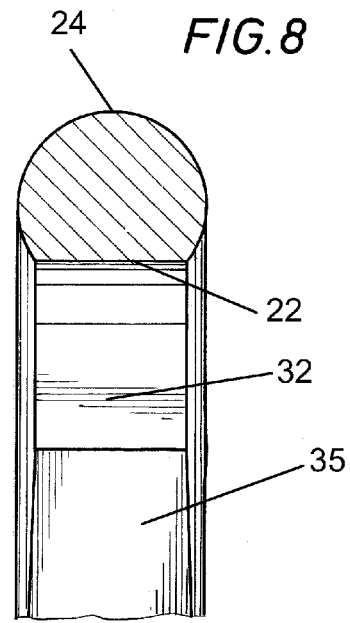
FIG. 8 is a view similar to that shown in FIG. 5, showing an alternate cross-section of the staple of the present invention

FIGS. 6-8 are similar to FIG. 5 but show alternative cross-sectional shapes of staple 10. As seen in FIGS. 5-8, the transverse cross-sectional shape can vary widely. FIG. 6 shows a transverse cross-section which is generally rectangular with rounded corners. FIG. 7 shows a more rounded transverse cross-section and FIG. 8 shows a transverse cross-section which is substantially circular but has a circular segment removed forming a flat inner surface 22. Each of these possible configurations have a flat inner surface, which grips the bone well, and a radiused, contoured outer surface which mitigates the irritation to the skin of the patient. It will be understood that other transverse cross-sectional shapes are contemplated by the present invention provided they have no abrupt surface changes, e.g., sharp corners or edges, on the outer surfaces.

Another advantage of the staple of the present invention resides in the fact that the surgeon can employ smaller diameter holes in the bone to implant the staple. In this regard, when repairing a bone fracture using staples of the type of the present invention, the surgeon will drill two holes on opposite sides of the fracture (see FIG. 3 for example). Desirably the holes will have as small a diameter as possible. In the case of prior art staples cut from sheets, the barbs, protrusions or the like extend laterally from the surfaces of the legs. Such barbs or protrusions may extend from the inner surface of the legs, the outer surface of the legs, or both. The result of such barbs, protrusions or the like extending laterally from the surface of the leg is that, at that location of the barb, the width of the leg, as measured from the laterally outermost point to the laterally innermost point, is substantially wider than the width of the leg without the barb. This necessitates that a larger hole be drilled in the bone by the surgeon.

This is to be contrasted with the staple of the present invention, wherein the thickness of the staple leg measured from the outermost surface, to the innermost tip of the barb, is not greater than the thickness of the wire from which the staple is formed. This is accomplished by grinding or otherwise removing material from the blank segment of the wire after it is cut to the desired length such that it provides a staple blank 10A, as shown in FIG. 9. As can be seen, when the staple blank 10A is formed into the staple 10, the legs 30 of the staples have tapered portions 35 occasioned by removal of the metal as discussed above. Thus over and above reducing the footprint of the staple at its point of insertion into the holes drilled into the bone, the taper facilitates insertion of the staple into the holes in the bone. It will be understood that blank 10A can be worked to form a plurality of barbs such that staple 10 would have a plurality of barbs on each leg 30 or a single barb on one leg and a plurality of barbs on the other leg 30.

Turning to FIG. 10, the grain lines G of the metal of staple 10 run along the length of the staple 10 from one foot 40 to the other foot 40 by virtue of the fact that staple 10 is formed from an extruded nickel/titanium alloy wire. In forming the staples 10, the extruded nickel/titanium alloy wire is cut into appropriate sized segments or blanks. In this regard, bone staples generally range from 8 mm to 25 mm in bridge length. The side of the wire blank which is to be the inner surface, i.e., the side which is not smooth or rounded, is then worked in a suitable manner to remove material from two portions of the blank to form tapered portions 35 (see FIG. 1), and feet 40 having barbs 41. The wire is then formed into the desired staple shape. Finally, to ensure the desired performance of the super elastic metal, the staples are thermally set at temperatures ranging from 400-600° C. The result is a super elastic staple having grain lines that run along the pathway of staple 10 from one foot 40 to the other foot 40. This pathway is indicated generally by lines G in FIG. 10.

Figure 11:
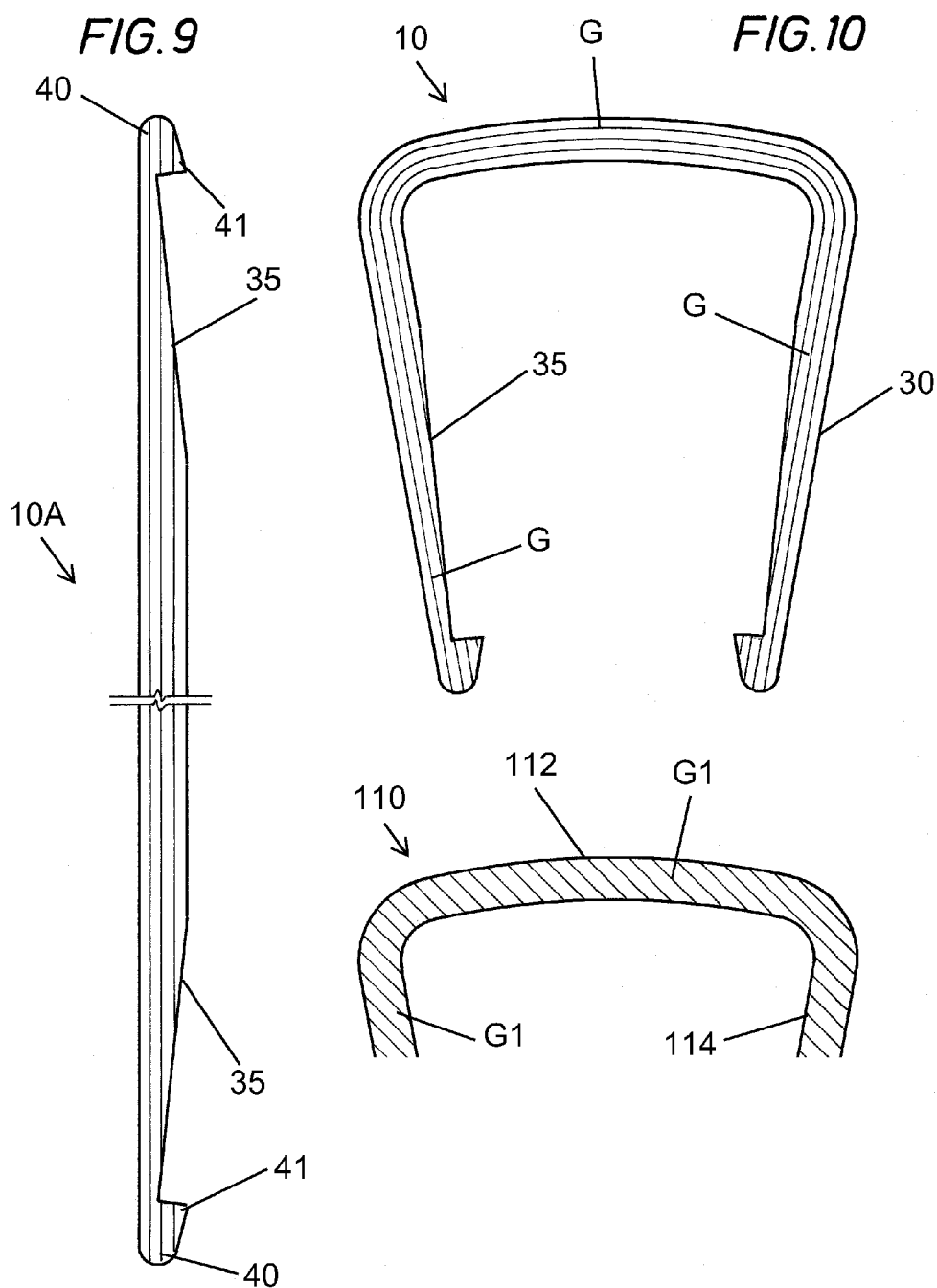
FIG. 11 is a view similar to FIG. 10, but showing how the grain lines of a prior art staple run.

FIG. 11 shows schematically how the grain lines of the metal run in a prior art staple 110, which has been laser cut from a sheet of nickel/titanium alloy. It can be seen that grain lines G1 running through staple 110 are transverse to the pathway G of FIG. 10, particularly at the intersections of the bridge 112 and the legs 114. Generally speaking, grain lines which are transverse to this intersection tend to set up stress risers which can compromise the integrity of the staple 110. In general, when cutting staples from a sheet, one obtains staples wherein the grain lines of the metal will be transverse to some part of the staple, including the intersections of the bridge and the legs. It will be appreciated that the prior art staples can be cut from the sheet such that the grain lines run in virtually any direction. However, no matter what the orientation of the staple cut from the sheet, at some point, the grain lines will be transverse to the pathway of the staple and more particularly to the intersection of the bridge and the leg. This is to be contrasted with the staples of the present invention and shown in FIG. 10 wherein the grain lines G are all running in such a fashion that they follow the pathway of the staple as opposed to being transverse to the pathway at any point.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A bone staple comprising:
   a generally U-shaped piece of super elastic metal having a bridge portion having first and second ends, and first and second legs depending from said first and second ends, respectively, said U-shaped piece having an inner surface and an outer surface;
   said outer surface of said U-shaped piece having radiused edges; and
   grain lines of said super elastic metal running longitudinally along said first leg, said bridge, and said second leg.

2. The bone staple of claim 1, wherein said inner and outer surfaces of said bridge portion define a cross-sectional thickness, and a portion of the inner surfaces of said first and second legs taper toward said outer surface, said first and second legs having first and second, inwardly projecting barbed formations, respectively, said formations having a cross-sectional thickness no larger than the cross-sectional thickness defined by said inner and outer surface of said bridge portion.

3. The bone staple of claim 2, wherein at least one of first and second legs has a plurality of inwardly projecting barbed formations.

4. The bone staple of claim 1, wherein said bridge portion is arcuate.

5. The bone staple of claim 1, wherein the bridge portion has a transverse cross-section which is generally rectangular with rounded corners.

6. The bone staple of claim 1, wherein the bridge portion has a transverse cross-section which is generally D-shaped, the inner surface of said bridge portion being substantially planar.

7. The bone staple of claim 1, wherein the bridge portion has a transverse cross-section which is substantially circular, and having a circular segment removed along the inner surface.

8. The bone staple of claim 1, wherein the staple is formed from an extruded length of wire.

9. A bone staple comprising:
   a generally U-shaped piece of memory metal having an inner surface, an outer surface, a bridge portion having first and second ends, a cross-sectional thickness defined by said inner and outer surfaces of said bridge portion, and first and second legs depending from said first and second ends of said bridge portion, respectively;
   said outer surface of said U-shaped piece being having radiused edges;
   a portion of the inner surfaces of said first and second legs tapering toward said outer surface, said first and second legs having first and second, inwardly projecting barbed formations, respectively; and
   grain lines of said memory metal running longitudinally along said first leg, said bridge, bridge, and said second leg.

10. The bone staple of claim 9, wherein at least one of first and second legs has a plurality of inwardly projecting barbed formations.

11. The bone staple of claim 9, wherein said bridge portion is arcuate.

12. The bone staple of claim 9, wherein the bridge portion has a transverse cross-section which is generally rectangular with rounded corners.

13. The bone staple of claim 9, wherein the bridge portion has a transverse cross-section which is generally D-shaped, the inner surface of said bridge portion being substantially planar.

14. The bone staple of claim 9 wherein the bridge portion has a transverse cross-section which is substantially circular, and having a circular segment removed along the inner surface.

15. The bone staple of claim 9, wherein the staple is formed of super elastic metal.

16. The bone staple of claim 9, wherein the staple is formed from an extruded piece of wire.

17. A bone staple comprising:
   a generally U-shaped piece of super elastic metal having an inner surface, an outer surface, a bridge portion having first and second ends, a cross-sectional thickness defined by said inner and outer surfaces of said bridge portion, and first and second legs depending from said first and second ends of said bridge portion, respectively;
   said outer surface of said U-shaped piece having radiused edges;
   a portion of the inner surfaces of said first and second legs tapering toward said outer surface, said first and second legs having first and second, inwardly projecting barbed formations, respectively, said formations having a cross-sectional thickness no larger than the cross-sectional thickness defined by said inner and outer surface of said bridge portion; and
   grain lines of said memory metal running longitudinally along said first leg, said bridge, and said second leg.

18. The bone staple of claim 17, wherein at least one of first and second legs has a plurality of inwardly projecting barbed formations.

19. The bone staple of claim 17, wherein the bridge portion has a transverse cross-section which is generally rectangular with rounded corners.

20. The bone staple of claim 17, wherein the bridge portion has a transverse cross-section which is generally D-shaped, the inner surface of said bridge portion being substantially planar.

21. The bone staple of claim 19, wherein the bridge portion has a transverse cross-section which is substantially circular, and having a circular segment removed along the inner surface.

22. The bone staple of claim 17, wherein said bridge portion is arcuate.

23. The bone staple of claim 17, wherein the staple is formed from an extruded piece of wire.

24. A bone staple comprising:
   a generally U-shaped piece of memory metal having an inner surface, an outer surface, a bridge portion having first and second ends, a cross-sectional thickness defined by said inner and outer surfaces of said bridge portion, and first and second legs depending from said first and second ends of said bridge portion, respectively;
   said outer surface of said U-shaped piece having radiused edges;
   a portion of the inner surfaces of said first and second legs tapering toward said outer surface, said first and second legs having first and second, inwardly projecting barbed formations, respectively, said formations having a cross-sectional thickness no larger than the cross-sectional thickness defined by said inner and outer surface of said bridge portion; and grain lines of said memory metal running longitudinally along said first leg, said bridge, and said second leg.

25. The bone staple of claim 24, wherein at least one of first and second legs has a plurality of inwardly projecting barbed formations.

26. The bone staple of claim 24, wherein the bridge portion has a transverse cross-section which is generally rectangular with rounded corners.

27. The bone staple of claim 24, wherein the bridge portion has a transverse cross-section which is generally D-shaped, the inner surface of said bridge portion being substantially planar.

28. The bone staple of claim 24, wherein the bridge portion has a transverse cross-section which is substantially circular, and having a circular segment removed along the inner surface.

29. The bone staple of claim 24, wherein said bridge portion is arcuate.

30. The bone staple of claim 24, wherein the staple is formed of super elastic metal.

31. The bone staple of claim 24, wherein the staple is formed from an extruded piece of wire.

* * * * *